United States Patent
Ouzounov

(10) Patent No.: US 10,941,406 B2
(45) Date of Patent: Mar. 9, 2021

(54) EXPRESSION OF PROTEINS IN GRAM-NEGATIVE BACTERIA WHEREIN THE RATIO OF PERIPLASMIC VOLUME TO CYTOPLASMIC VOLUME IS BETWEEN 0.5:1 AND 10:1

(71) Applicant: Geltor, Inc., San Leandro, CA (US)

(72) Inventor: Nikolay Ouzounov, Alameda, CA (US)

(73) Assignee: GELTOR, INC., San Leandro, CA (US)

( * ) Notice: Subject to any disclaimer, the term of this patent is extended or adjusted under 35 U.S.C. 154(b) by 0 days.

(21) Appl. No.: 16/088,797

(22) PCT Filed: Mar. 29, 2017

(86) PCT No.: PCT/US2017/024857
§ 371 (c)(1),
(2) Date: Sep. 26, 2018

(87) PCT Pub. No.: WO2017/172994
PCT Pub. Date: Oct. 5, 2017

(65) Prior Publication Data
US 2019/0106702 A1    Apr. 11, 2019

Related U.S. Application Data

(60) Provisional application No. 62/314,924, filed on Mar. 29, 2016.

(51) Int. Cl.
*C12P 21/02* (2006.01)
*C12N 15/70* (2006.01)
(Continued)

(52) U.S. Cl.
CPC .............. *C12N 15/70* (2013.01); *C07K 14/78* (2013.01); *C07K 16/00* (2013.01); *C12N 1/20* (2013.01);
(Continued)

(58) Field of Classification Search
None
See application file for complete search history.

(56) References Cited

U.S. PATENT DOCUMENTS 6,180,367 B1 *   1/2001   Leung .................. C07K 14/005
                                                435/252.1
6,413,742 B1    7/2002   Olsen et al.
(Continued)

FOREIGN PATENT DOCUMENTS

CN    101410523 A    4/2009
EP    1 323 820 A    7/2003
(Continued)

OTHER PUBLICATIONS

Winter et al., "Increased production of human proinsulin in the periplasmic space of *Escherichia coli* by fusion to DsbA", Journal of Biotechnology, vol. 84, pp. 175-185, 2000 (Year: 2000).*
(Continued)

*Primary Examiner* — Richard C Ekstrom
(74) *Attorney, Agent, or Firm* — Wilson Sonsini Goodrich & Rosati

(57) ABSTRACT

Provided are modified Gram-negative bacteria having an increased periplasmic volume. Also provided are methods of expressing exogenous genes in the bacteria and targeting protein production to the periplasmic space.

25 Claims, 4 Drawing Sheets

(51) Int. Cl.
    *C07K 14/78*     (2006.01)
    *C12N 1/20*     (2006.01)
    *C12N 15/67*     (2006.01)
    *C07K 16/00*     (2006.01)

(52) U.S. Cl.
    CPC .............. *C12N 15/67* (2013.01); *C12P 21/02* (2013.01); *C07K 2317/14* (2013.01); *C07K 2319/02* (2013.01)

(56) References Cited

U.S. PATENT DOCUMENTS

| | | | |
|---|---|---|---|
| 6,428,978 | B1 | 8/2002 | Olsen et al. |
| 7,754,447 | B2 | 7/2010 | Glover et al. |
| 8,618,250 | B2 | 12/2013 | Russell et al. |
| 9,243,253 | B2 * | 1/2016 | Retallack .............. C12P 21/02 |
| 9,267,164 | B2 * | 2/2016 | O'Keefe ............ G01N 33/5008 |
| 9,725,498 | B2 | 8/2017 | Russell et al. |
| 9,962,582 | B2 | 5/2018 | Antku |
| 2013/0237486 | A1 | 9/2013 | Bella |
| 2019/0106702 | A1 * | 4/2019 | Ouzounov ............. C07K 16/00 |

FOREIGN PATENT DOCUMENTS

| | | |
|---|---|---|
| WO | WO-03106494 A1 | 12/2003 |
| WO | 2016-004334 A1 | 1/2016 |
| WO | WO-2017172994 A1 | 10/2017 |

OTHER PUBLICATIONS

Chen et al. Construction of leaky strains and extracellular production of exogenous proteins in recombinant *Escherichia coli*. Microbiol Biotechnology 7(4):360-370 (Jul. 2014).

Choi and Lee, Secretory and extracellular production of recombinant proteins using *Escherichia coli*. Appl. Microbiol. Biotechnol. 64:625-635, 2004.

Dinh et al. Using superfolder green fluorescent protein for periplasmic protein localization studies. J Bacteriol 193(18):4984-4987 (Sep. 2011). Epub Jul. 15, 2011. doi: 10.1128/JB.00315-11.

Fernández et al. Specific Secretion of Active Single-Chain Fv Antibodies into the Supernatants of *Escherichia coli* Cultures by Use of the Hemolysin System. Appl Environ Microbiol 66(11):5024-5029 (Nov. 2000).

Fu et al., Extracellular production of human parathyroid hormone as a thioredoxin fusion form in *Escherichia coli* by chemical permeabilization combined with heat treatment. Biotechnol. Prog., 21:1429-1435, 2005.

Fu. Extracellular accumulation of recombinant protein by *Escherichia coli* in a defined medium. Appl Microbiol Biotechnol 88(1):75-86 (Sep. 2010). Epub Jun. 24, 2010.

Gumpert et al. Characteristic properties and biological significance of stable protoplast type L-forms. In Protoplasts, Lecture Proceedings of the 6th International Protoplast Symposium: Basel. Experientia 1983, 46(suppl):227-241.

Gumpert et al. Use of cell wall-less bacteria (L-forms) for efficient expression and secretion of heterologous gene products. Current Opinion in Biotechnology 9(5):506-509 (Oct. 1998).

Hoischen et al. Lipid and fatty acid composition of cytoplasmic membranes from Streptomyces hygroscopicus and its stable protoplast-type L form. J Bacteriol 179(11):3430-3436 (Jun. 1997).

Jeong K.J. and Lee S.Y., "Excretion of Human β-Endorphin into Culture Medium by Using Outer Membrane Protein F as a Fusion Partner in Recombinant *Escherichia coli*," 2002, Appl. Environ. Microbio 68: vol. 10, pp. 4979-4985.

Joly et al. Chapter 20: Practical Applications for Periplasmic Protein Accumulation, in The Periplasm, ed. Ehrmann, M., ASM Press, Washington D.C., pp. 345-360 (2007).

Koebnik et al. Structure and function of bacterial outer membrane proteins: barrels in a nutshell. Mol Microbiol 37(2):239-253 (2000).

Makrides. Strategies for achieving high-level expression of genes in *Escherichia coli*. Microbiolog Rev 60(3):512-538 (1996).

Mecham et al. Methods in elastic tissue biology: Elastin isolation and purification. Methods 45(1):32-41 (May 1, 2008).

Mergulhao et al., Recombinant protein secretion in *Escherichia coli*. Biotechnology Advances, 23:177-202, 2005.

Orr et al. Integrated development of an effective bioprocess for extracellular production of penicillin G acylase in *Escherichia coli* and its subsequent one-step purification. J Biotechnol 161(1):19-26 (Sep. 15, 2012). Available online Jun. 20, 2012.

Qian et al. Proteome-based identification of fusion partner for high-level extracellular production of recombinant proteins in *Escherichia coli*. Biotechol Bioeng 101(3):587-601 (Oct. 15, 2008). Published online Mar. 19, 2008.

Rinas et al. Selective Leakage of Host-Cell Proteins during High-Cell-Density Cultivation of Recombinant and Non-recombinant *Escherichia coli*. Biotechnol Prog 20(3):679-687 (2004). Published online Feb. 14, 2004.

Robbens et al. Production of Soluble and Active Recombinant Murine Interleukin-2 in *Escherichia coli*: High Level Expression, Kil-Induced Release, and Purification.Protein Expr Purif 6(4):481-486 (1995).

Shin et al. Extracellular recombinant protein production from an *Escherichia coli* lpp deletion mutant. Biotechnol Bioeng 101(6):1288-1296 (Dec. 15, 2008). Published online Jun. 16, 2008.

Shokri et al. Cell and process design for targeting of recombinant protein into the culture medium of *Escherichia coli*. Appl Microbiol Biotecnol 60(6):654-664 (Feb. 2003). Published online Dec. 14, 2002.

Sugamata et al. Improved Secretory Production of Recombinant Proteins by Random Mutagenesis of hlyB, an Alpha-Hemolysin Transporter from *Escherichia coli*. Appl Env Microbiol 71(2):656-662 (Feb. 2005).

Takemori et al. Extracellular production of phospholipase A2 from Streptomyces violaceoruber by recombinant *Escherichia coli*. Protein Expr Purif 81:145-150 (Feb. 2012). Available online Oct. 14, 2011.

Van Der Wal et al. Optimization of bacteriocin-release-protein-induced protein release by *Escherichia coli*: extracellular production of the periplasmic molecular chaperone FaeE. Appl Microbiol Biotechnol 44(3-4):459-465 (1995).

Yang et al. One Hundred Seventy-Fold Increase in Excretion of an FV Fragment-Tumor Necrosis Factor Alpha Fusion Protein (sFV/TNF-α) from *Escherichia coli* Caused by the Synergistic Effects of Glycine and Triton X-100. Appl Environ Microbiol 64(8):2869-2874 (Aug. 1998).

Zhang et al. Extracellular accumulation of recombinant proteins fused to the carrier protein YebF in *Escherichia coli*.Nature Biotechnology 24(1):100-104 (Jan. 2006). Epub Dec. 20, 2005.

Cayley, D. Scott, et al., "Biophysical characterization of changes in amounts and activity of *Escherichia coli* cell and compartment water and turgor pressure in response to osmotic stress", Biophysical Journal, (Apr. 2000), 78(4):1748-1764.

Gortz, H. —D. et al., "Changes in Fine Structure and Polypeptide Pattern during Development of Holospora obtuse, a bacterium Infecting the macronucleus of Paramecium caudatum", Journal of Bacteriology, (Oct. 1, 1990), 172(10):5664-5669, XP055373233, Retrieved from the Internet: URL: https://www.ncbi.nlm.nih.gov/pmc/articles/PMC526880/pdf/jbacter00164-0156.pdf, [retrieved May 16, 2017].

Haworth, R.S. et al., "Uncoupler resistance in *E. Coli* Tuv and Cuv is due to the exclusion of uncoupler by the outer membrane", *Biochim Biophys Acta.*, (Aug. 9, 1990), 1019(1):67-72, XP023349580, ISBN: 0005-2728, DOI: 10.1016/0005-2728(90)90125-N [retrieved on Aug. 9, 1990].

Pilizota, Teuta and J. W. Shaevitz, "Fast, Multiphase Volume Adaptation to Hyperosmotic Shock by *Escherichia coli*", PLoS ONE, (Apr. 2012), 7(4): e35205. https://doi.org/10.1371/journal.pone.0035205.

International Search Report and Written Opinion of the Searching Authority for International Patent Application No. PCTT/US2017/024857, dated May 31, 2017, 12 pages.

(56) References Cited

OTHER PUBLICATIONS

International Preliminary Report on Patentability, dated Oct. 11, 2018, for International Patent Application No. PCTT/US2017/024857, 10 pages.

* cited by examiner

EXPRESSION OF PROTEINS IN GRAM-NEGATIVE BACTERIA WHEREIN THE RATIO OF PERIPLASMIC VOLUME TO CYTOPLASMIC VOLUME IS BETWEEN 0.5:1 AND 10:1

CROSS-REFERENCE TO RELATED APPLICATIONS AND APPLICATIONS INCORPORATED BY REFERENCE

This application is a National Phase application of International Patent Application No. PCT/US17/24857, filed Mar. 29, 2017, entitled "EXPRESSION OF PROTEINS IN GRAM-NEGATIVE BACTERIA WHEREIN THE RATIO OF PERIPLASMIC VOLUME TO CYTOPLASMIC VOLUME IS BETWEEN 0.5:1 AND 10:1", which claims priority from U.S. Provisional Patent Application 62/314,924, filed Mar. 29, 2016, titled MODIFIED BACTERIA AND USES THEREOF; the disclosures of which are incorporated by reference herein in their entirety.

BACKGROUND

Field

The invention relates to modified Gram-negative bacteria having an increased periplasmic volume, and methods of expressing exogenous genes therein. The bacteria are useful for targeting recombinant protein production to the periplasmic space.

Description of the Related Art

In spite of longstanding efforts to optimize prokaryotic expression systems, a number of obstacles still remain to obtaining sufficient yields of functionally active gene products, including the formation of inclusion bodies, incorrect folding of the expressed protein, toxicity for the producer cells and degradation by proteases. A variety of alternative expression systems are being developed and evaluated to produce recombinant proteins more effectively.

*Escherichia coli* is the most commonly used host for the production of recombinant proteins. In order to obtain the target exogenous proteins expressed intracellularly in recombinant *E. coli*, however, cell disruption is necessary, which can increase of pyrogen level (mainly from the cell membrane composition), increase sample impurities and decrease protein activities. Particularly, the formation of inclusion bodies often occurs when the target protein is intracellularly overexpressed. To overcome these problems, extracellular secretion of exogenous proteins in recombinant *E. coli* is becoming an increasingly popular choice. In large-scale industrial production of exogenous proteins, the extracellular excretion of target proteins can remove the cell disruption step, offer a better environment for protein folding and reduce the risk of intracellular enzyme degradation (Mergulhao et al., 2005, Biotechnol Adv 23: 177-202). Additionally, the extracellular secretion of target proteins can improve the recombinant protein yield because the target protein accumulation is not limited in periplasmic or intracellular space (Makrides, 1996, Microbiol Rev 60: 512-538; Fu et al., 2005, Biotechnol Prog 21: 1429-1435).

The primary challenge with the extracellular secretion of recombinant proteins are the difficulties inherent in protein translocation across both the cell membrane and the outer membrane of *E. coli* cells (Koebnik et al., 2000, Mol Microbiol 37: 239-253; Choi and Lee, 2004, Appl Miccro-biol Biotechnol 64: 625-635). While periplasmic expression of recombinant proteins can often be achieved with the help of a signal peptide, the available methods to overcome the outer membrane barrier for extracellular production of recombinant proteins are much more limited. In order to solve this problem, various genetic attempts have been made to facilitate the extracellular secretion of recombinant proteins in *E. coli*, including manipulation of transport pathways (Sugamata and Shiba, 2005, Appl Environ Microbiol 71: 656-662), optimization of codon and signal sequence (Takemori et al., 2012, Protein Expr Purif 81: 145-150), fusion expression of carrier protein which can be normally secreted extracellularly (Fernandez et al., 2000, Appl Environ Microbiol 66: 5024-5029; Choi and Lee, 2004) and fusion expression of outer membrane protein F (Jeong and Lee, 2002, Appl Environ Microbiol 68: 4979-4985), YebF (Zhang et al., 2006, Nat Biotechnol 24: 100-104) or osmotically inducible protein Y (Qian et al., 2008, Biotechnol Bioeng 101: 587-601). In addition, the coexpression of lysis-promoting proteins such as bacteriocin release protein (BRP) (van der Wal et al., 1995, Appl Microbiol Biotechnol 44: 459-465) or colicin E1 lysis protein (Kil) (Robbens et al., 1995, Protein Expr Purif 6" 481-486), as well as the use of wall-less strains (the so-called L-forms) (Gumpert and Hoischen, 1998, Current Opinion in Biotechnology, 9: 506-509) have also been reported.

Meanwhile, many fermentation techniques, including changes of culture medium compositions (Fu, 2010, Appl Microbiol Biotechnol 88: 75-86), temperature (Rinas and Hoffmann, 2004, Biotechnol Prog, 20: 679-687), aeration and calcium ion (Shokri et al., 2003, Appl Microbiol Biotechnol 60: 654-664), osmotic pressure and induction conditions (Orr et al., 2012, J Biotechnol 161, 19-26), as well as the addition of supplements such as glycine (Yang et al., 1998, Appl Environ Microbiol 64: 2869-2874) and Triton X-100 (Fu et al., 2005, Biotechnol Prog 21: 1429-1435; Fu, 2010), have been explored to achieve the extracellular production of recombinant proteins in *E. coli*. The main disadvantage of the fermentation control for the extracellular production of target proteins is that the fermentation conditions vary greatly with different target proteins.

Leaky strains (including the *E. coli* Sec pathway) offer an alternative means for transporting periplasmic-directed recombinant proteins into media that overcomes the uncertainty of the fermentation conditions. Leaky strains can be constructed by knocking out genes related to the biosynthesis of cell wall and membrane, especially of the outer membrane genes such as lpp encoding Braun's lipoprotein (Shin and Chen, 2008, Biotechnol Bioeng 101: 1288-1296) of *E. coli*. More recently, Chen et al. (Microbial Biotechnology, 2014, 7, 360-370) constructed several leaky strains of *E. coli* JM109 (DE3), including mrcA, mrcB, pal and lpp (single-gene knock-out), and lpp mrcB, mrcA lpp, lpp pal, mrcA pal and mrcB pal (double-gene knock-out), by an inframe deletion method to improve the extracellular secretory levels of their target proteins. Extracellular yields of recombinant protein Trx-hPTH (human parathyroid hormone 1-84 coupled with thioredoxin as a fusion partner) from the mutants with double deletion were significantly higher than those from the mutants with single deletion under the same conditions. In addition, mutants with inframe single/double deletion of genes, mrcB and lpp, could not cause the efficient leakage of the target protein due to protein expression in the cytoplasm rather than the periplasm. Accordingly, while the main advantage of leaky strains is that no additives are needed to induce extracellular protein production, the main disadvantage is that their secretory selectivity is not high, suggesting that these genes affect the structure of the outer membrane but do not participate in the active transport of target protein(s).

L-form bacteria, or L-forms, are bacterial strains derived from parent species (N-forms) that are able to grow as cell wall-deficient (spheroplast type) or as cell wall-less (protoplast type) cells. See, Madoff S (Ed): The Bacterial L-Forms. New York: Marcel Dekker Inc., 1986; Mattmann L H (Ed): Cell Wall Deficient Forms. Boca Raton: CRC Press; 1993; and Gumpert J, Taubeneck U: Characteristic properties and biological significance of stable protoplast type L-forms. In Protoplasts, Lecture Proceedings of the 6$^{th}$ International Protoplast Symposium: Basel. Experientia 1983, 46(suppl): 227-241.

Protoplast type L-forms have been cultivated in the cell wall-less state and represent genetically stable mutants showing extreme pleiotropic changes, including the inability to form cell walls, capsules, flagella, pili, spores and mesosomes, altered colony and cell morphology, qualitative and quantitative changes in the lipid and protein components of the cytoplasmic membrane, the absence of extracelluar proteolytic activities, resistance against bacteriophages and the incapability to propagate outside laboratory conditions. See, Gumpert and Taubeneck (supra); and Hoischen et al., Lipid and fatty acid composition of cytoplasmic membranes from *Streptomyces hygroscopicus* and its stable protoplast type L-form. J Bacteriol 1997, 179:3430-3436.

Gumpert and Hoischen (Current Opinion in Biotechnology, 1998, 9:506-509) describe expression systems in which cell wall-less L-form strains of *Proteus mirabilis*, *Escherichia coli*, *Bacillus subtilis*, and *Streptomyces hydroscopicus* were used to synthesize various recombinant proteins in considerable amounts as soluble, functionally active products. The recombinant proteins were secreted by the L-form cells into the surrounding growth medium by an active translocation process that required appropriate signal peptides. Among the proteins synthesized were correctly processed antibodies and miniantibodies, indicating that the appropriate post-translational modifications (correct folding, formation of disulfide bonds, and dimerization) had occurred. The authors noted that because the L-form strains lacked a periplasmic compartment this is not a necessary prerequisite for post-translational processing and that the cytoplasmic membrane of the L-form cells plays a role in these modification processes. The L-form cells were more sensitive to environmental influences than widely-used *E. coli* expression systems and they needed more careful handling, in particular, control of the inoculum, the avoidance of contacts with membrane-active surfactants and other aggressive substances, and complex growth media. The authors concluded that the most important advantage of their L-form expression system was the removal of the synthesized protein by active translocation through the cytoplasmic membrane and secretion into the surrounding growth medium, and that it was probably not useful for large scale fermentations.

Accordingly, there is clearly still a need for improved methods for the fermentative preparation of proteins. The recombinant bacteria, cell culture media, and processes described herein help meet these and other needs.

BRIEF SUMMARY

The present invention solves the foregoing problems in the prior art by providing compositions and methods for the enhanced periplasmic production of recombinant proteins. In particular, modified bacterial cells are provided exhibiting a novel physiological state which inhibits cell division and promotes the growth of the periplasmic space in comparison to the cytoplasmic space. As demonstrated for the first time herein, recombinant protein production in these cells is dramatically increased compared with that in non-switched cells. Structurally, the cells comprise both inner and outer membranes but lack a functional peptidoglycan cell wall, while the cell shape is spherical and increases in volume over time. Notably, while the periplasmic space normally comprises only 10-20% of the total cell volume, the periplasmic compartment of the switched state described herein can comprise more than 20%, 30%, 40% or 50% and up to 60%, 70%, 80% or 90% of the total cell volume. In some cases, this increased periplasmic space provides for dramatically increased expression of recombinant proteins into the periplasmic space.

In one aspect, modified bacterial cells are provided exhibiting this switched phenotype, where the periplasmic space in the subject bacterial cells comprises at least about 20% or 25% of the total cell volume, more preferably at least about 30%, 35%, 40%, or 45% of the total cell volume, still more preferably at least about 50%, 55%, 60%, 65%, or 70% of the total cell volume, and most preferably at least about 75%, 80%, 85% or 90% of the total cell volume.

Preferably, the modified bacterial cells of the subject invention are derived from Gram-negative bateria, e.g. selected from: gammaproteobacteria and alphaproteobacteria. In particularly preferred embodiments, the bacterium is selected from: *Escherichia coli*, *Vibrio natriegens*, *Pseudomonas fluorescens*, *Caulobacter crescentus*, *Agrobacterium tumefaciens*, and *Brevundimonas diminuta*. In specific embodiments, the bacterium is *Escherichia coli*, e.g. strain BL21, BL21(DE3), or K12.

In some embodiments, the modified bacterial cells according to the present invention have a ratio of periplasmic volume to cytoplasmic volume between about 0.5:1 and about 10:1, between about 0.5:1 and about 5:1, between about 0.5:1 and about 1:1, between about 1:1 and about 10:1, between about 1:1 and about 5:1, or between about 5:1 and about 10:1.

In some embodiments, a modified bacterial cell of the present invention is a coccus having a longest dimension of about 2 µm to about 16 µm, more preferably about 4 µm to about 16 µm, still more preferably about 8 µm to about 16 µm, or about 2 µm to about 8 µm, or about 4 µm to about 8 µm, or about 2 µm to about 4 µm.

Preferably, the modified bacterial cells of the subject invention further comprise an exogenous gene encoding a protein of interest. Proteins of interest can be therapeutic, e.g., antibodies, hormones, growth factors, vaccines, and any other functional and/or structural proteins and enzymes of medical interest, as well as non-therapeutic, e.g., collagen and derivatives thereof, albumin, ovalbumin, rennet, fibrin, casein (including αS1, αS2, β, κ), elastin, keratin, myosin, fibronectin, laminin, nidogen-1, vitronectin, silk fibroins, prolyl hydroxylases, lysyl hydroxylases, glycosyltransferases, hemeproteins, and any other structural or non-structural proteins or enzymes of commercial and/or academic interest. Proteins of interest herein may exclude fluourescent proteins. In certain embodiments, the protein is other than mCherry or green fluorescent protein.

In one embodiment, the exogenous gene is integrated into the host bacterial cell genome. In another embodiment, the bacterial cell comprises an expression vector comprising the exogenous gene. In some embodiments, the expression vector is free of a marker encoding for resistance to an inhibitor of bacterial cell peptiglycan biogenesis. In an exemplary embodiment, the expression vector comprises a pET plasmid. In a particular embodiment, the expression vector comprises plasmid pET28a.

In one embodiment, expression of the exogenous gene is constitutive. In another embodiment, expression of the exogenous gene is inducible. In some embodiments, expression of the exogenous gene is inducible by an inducer selected from, e.g. isopropyl-β-d-1-thiogalactopyranoside, lactose, arabinose, maltose, tetracycline, anhydrotetracycline, vavlycin, xylose, copper, zinc, and the like.

In one embodiment, the modified bacterial cells further comprise a nucleic acid sequence encoding a signal peptide operably linked to the exogenous gene, wherein the signal peptide directs cotranslational export of the protein from the cytoplasm to the periplasm. In some embodiments, the signal peptide is derived from a protein component of the Sec and Tat secretion pathways. In particular embodiments, the signal peptide is derived from DsbA, pelB, OmpA, TolB, MalE, lpp, TorA, or HylA. For example, the signal peptide can be an N-terminal portion of DsbA, pelB, OmpA, TolB, MalE, lpp, TorA, or HylA that directs cotranslational export of the protein from the cytoplasm to the periplasm. In some cases, the signal peptide can contain at least 10%, 25%, 50%, 75%, 95%, 99%, or all of a peptide selected from DsbA, pelB, OmpA, TolB, MalE, lpp, TorA, or HylA.

In some embodiments, the modified bacterial cell comprises a coccus form of an ampicillin sensitive (amp$^S$) and/or fosfomycin-sensitive bacillus strain, wherein the coccus form and the bacillus strain are genetically identical.

In another aspect, cell cultures are provided comprising bacterial cells having an enlarged periplasmic space in a culture medium comprising a magnesium salt, wherein the concentration of magnesium ions in the medium is at least about 4, 5 or 6 mM. In further embodiments, the concentration of magnesium ions in the medium is at least about 7, 8, 9 or 10 mM. In some embodiments, the concentration of magnesium ions in the medium is between about 6 mM and about 20 mM. In some embodiments, the magnesium salt is selected from: magnesium sulfate and magnesium chloride.

Preferably, the cell culture of the subject invention further comprises an osmotic stabilizer, including, e.g. sugars (e.g., arabinose, glucose, sucrose, glycerol, sorbitol, mannitol, fructose, galactose, saccharose, maltotrioseaerythritol, ribitol, pentaerythritol, arabitol, galactitol, xylitol, iditol, maltotriose, and the like), betaines (e.g., trimethylglycine), proline, one or more salts such as an ammonium, potassium, or sodium salt (e.g., sodium chloride), one or more polymers (e.g., polyethylene glycol, polyethylene glycol monomethylether, polysucrose, polyvinylpyrrolidone, polypropylene glycol), or a combination thereof. In some cases, the concentration of the osmotic stabilizer(s) in the medium is at least about 4%, 5%, 6%, or 7% (w/v). In further embodiments, the concentration of osmotic stabilizer is at least about 8%, 9%, or 10% (w/v). In some embodiments, the concentration of the osmotic stabilizer in the medium is between about 5% to about 20% (w/v).

In some embodiments, the cell culture may further comprise ammonium chloride, ammonium sulfate, calcium chloride, amino acids, iron(II) sulfate, magnesium sulfate, peptone, potassium phosphate, sodium chloride, sodium phosphate, and yeast extract. In some embodiments, the cell culture is free of animal-derived components. In some embodiments, the cell culture comprises, consists essentially of, or is in, a defined medium.

In some embodiments, the cell culture comprises from about $1\times10^8$ bacterial cells per mL of culture volume to about $1\times10^{10}$ bacterial cells per mL in a volume of at least about 1 L (e.g., from about 1 L to about 500,000 L, from about 1 L to about 10,000 L, from about 1 L to about 1,000 L, from about about 1 L to about 500 L, or from about 1 L to about 250 L). In some embodiments, the cell culture comprises from about $4\times10^8$ bacterial cells per mL of culture volume to about $1\times10^9$ bacterial cells per mL in a volume of at least about 1 L (e.g., from about 1 L to about 500,000 L, from about 1 L to about 10,000 L, from about 1 L to about 1,000 L, from about about 1 L to about 500 L, or from about 1 L to about 250 L).

In some embodiments, the cell culture comprises at least one exogenous antibiotic inhibitor of bacterial cell peptidoglycan biogenesis. In some embodiments, the cell culture comprises at least two structurally distinct exogenous antibiotic inhibitors of bacterial cell peptidoglycan biogenesis. In some cases, the at least two structurally distinct exogenous antibiotic inhibitors of bacterial cell peptidoglycan biogenesis inhibit different components of a peptidoglycan biogenesis pathway in the bacterial cell (e.g., the at least two structurally distinct exogenous antibiotic inhibitors inhibit different enzymes of the peptidoglycan biogenesis pathway in the bacterial cell). In some cases, the cell culture comprises an exogenous antibiotic inhibitor of a transglycosylase component of bacterial cell peptidoglycan biogenesis. In some cases, the cell culture comprises an exogenous antibiotic inhibitor of a transpeptidase component of bacterial cell peptidoglycan biogenesis. In some cases, the cell culture comprises an exogenous antibiotic inhibitor of UDP-N-acetylmuramyl (UDP-MurNAc)-pentapeptide biogenesis or UDP-N-acetylglucosamine (UDP-GlcNAc) biogenesis.

In some cases, the cell culture comprises an exogenous antibiotic inhibitor of MurA, MurB, MurC, MurD, MurE, MurF, MraY, MurG, FemX, FemA, FemB, FtsW, or a penicillin binding protein (PBP). In some cases, the cell culture comprises at least two structurally distinct exogenous antibiotic inhibitors, wherein the at least two structurally distinct exogenous antibiotic inhibitors inhibit different proteins selected from MurA, MurB, MurC, MurD, MurE, MurF, MraY, MurG, FemX, FemA, FemB, FtsW, or a penicillin binding protein (PBP). In some embodiments, the cell culture comprises at least one or at least two structurally distinct antibiotic(s) selected from: β-lactam antibiotics, phosphonic acid antibiotics, polypeptide antibiotics, D-cycloserine, and glycopeptide antibiotics, wherein the antibiotic(s) inhibit peptidoglycan biogenesis in the bacterial cell.

In some embodiments, the culture medium comprises at least one reactive oxygen species (ROS) scavenger (e.g., reduced glutathione (GSH), or a thiol containing non-peptidic small molecule having a molecular weight from about 70 g/mol to about 350 g/mol, or from about 75 g/mol to about 155 g/mol).

In some embodiments, the culture medium comprises an antibiotic (e.g., second or third antibiotic) that selects for the presence of a selectable marker in an expression vector that comprises an exogenous gene encoding for a protein of interest. In some embodiments, the antibiotic that selects for the presence of a selectable marker in the expression vector is not an inhibitor of peptidoglycan biogenesis in the bacterial cell.

In another aspect, methods of producing an exogenous protein of interest are provided (e.g., using one or more of the foregoing cell cultures and/or bacterial cells), comprising: a) culturing a Gram-negative bacterial cell in a medium comprising a magnesium salt, wherein the concentration of magnesium ions in the culture medium is at least about 4, 5 or 6 mM, and wherein the bacterial cell comprises an exogenous gene encoding the protein of interest; b) inhibiting peptidoglycan biogenesis in the bacterial cell; and c) harvesting the protein from the medium. In further embodiments, the concentration of magnesium ions in the medium is at least about 7, 8, 9 or 10 mM. In some embodiments, the concentration of magnesium ions in the medium is between about 6 mM and about 20 mM. In some embodiments, the magnesium salt is selected from: magnesium sulfate and magnesium chloride. In some embodiments, the culturing of a), or a portion thereof and/or the inhibiting of b), or a portion thereof is performed in one or more of the foregoing cell cultures. In some embodiments, expression of the exogenous gene encoding the protein of interest is induced, e.g., by adding an inducer to the medium, during step b). In some embodiments, expression of the exogenous gene encoding the protein of interest is induced, e.g., by adding an inducer to the medium, before step b). In some embodiments, expression of the exogenous gene encoding the protein of interest is induced, e.g., by adding an inducer to the medium, after step b) has been initiated.

Preferably, the cell culture of the subject invention further comprises an osmotic stabilizer, including, e.g. sugars (e.g., arabinose, glucose, sucrose, glycerol, sorbitol, mannitol, fructose, galactose, saccharose, maltotrioseerythritol, ribitol, pentaerythritol, arabitol, galactitol, xylitol, iditol, maltotriose, and the like), betaines (e.g., trimethylglycine), proline, one or more salts such as an ammonium, potassium, or sodium salt (e.g., sodium chloride), one or more polymers (e.g., polyethylene glycol, polyethylene glycol monomethylether, polysucrose, polyvinylpyrrolidone, polypropylene glycol), or a combination thereof. In some cases, the concentration of the osmotic stabilizer(s) in the medium is at least about 4%, 5%, 6%, or 7% (w/v). In further embodiments, the concentration of osmotic stabilizer is at least about 8%, 9%, or 10% (w/v). In some embodiments, the concentration of the osmotic stabilizer in the medium is between about 5% to about 20% (w/v).

In some embodiments, the cell culture may further comprise ammonium chloride, ammonium sulfate, calcium chloride, amino acids, iron(II) sulfate, magnesium sulfate, peptone, potassium phosphate, sodium chloride, sodium phosphate, and yeast extract.

The bacterial cell may be cultured continuously or discontinuously; in a batch process, a fed-batch process or a repeated fed-batch process. In some embodiments, steps b) and c) occur sequentially. In other embodiments, steps b) and c) occur simultaneously. In some embodiments, step c) is performed at least 1 hour after step b).

In some embodiments, the inhibiting peptidoglycan biogenesis in the bacterial cell is performed by adding an antibiotic to the medium. In some cases, the inhibiting peptidoglycan biogenesis in the bacterial cell is performed by adding two or more structurally distinct antibiotics to the medium. In some cases, the antibiotic or antibiotics are selected from: β-lactam antibiotics (e.g. penicllins, cephalosporins, carbapenems, and monobactams), phosphonic acid antibiotics, polypeptide antibiotics, and glycopeptide antibiotics. In particular embodiments, the antibiotic or antibiotics are selected from alafosfalin, amoxicillin, ampicillin, aztreonam, bacitracin, carbenicillin, cefamandole, cefotaxime, cefsulodin, cephalothin, fosmidomycin, methicillin, nafcillin, oxacillin, penicillin g, penicillin v, fosfomycin, primaxin, D-cycloserine, and vancomycin. In some embodiments, the antibiotic or antibiotics are selected from inhibitors of MurA, MurB, MurC, MurD, MurE, MurF, MraY, MurG, FemX, FemA, FemB, FtsW, or a penicillin binding protein (PBP). In some embodiments, the inhibiting peptidoglycan biogenesis in the bacterial cell is performed by adding an inhibitor of MurA and an inhibitor of a penicillin binding protein (PBP) to the medium. In some embodiments, the inhibiting peptidoglycan biogenesis in the bacterial cell is performed by adding an inhibitor of MurA to the medium. In some embodiments, the inhibiting peptidoglycan biogenesis in the bacterial cell is performed by adding an inhibitor of PBP to the medium.

Preferably, the modified bacterial cells of the subject invention are derived from Gram-negative bateria, e.g. selected from: gammaproteobacteria and alphaproteobacteria. In particularly preferred embodiments, the bacterium is selected from: *Escherichia coli, Vibrio natriegens, Pseudomonas fluorescens, Caulobacter crescentus, Agrobacterium tumefaciens*, and *Brevundimonas diminuta*. In specific embodiments, the bacterium is *Escherichia coli*, e.g. strain BL21(DE3).

In one embodiment, the exogenous gene is integrated into the host bacterial cell genome. In another embodiment, the bacterial cell comprises an expression vector comprising the exogenous gene. In some embodiments, the medium comprises an antibiotic that selects for the presence of the expression vector. In some embodiments, the antibiotic that selects for the presence of the expression vector is not an inhibitor of peptidoglycan biogenesis in the bacterial cell. In an exemplary embodiment, the expression vector comprises a pET plasmid. In a particular embodiment, the expression vector comprises plasmid pET28a.

In a further embodiment, the subject methods comprise inducing expression of the exogenous gene. In some embodiments, expression of the exogenous gene is inducible by an inducer selected from, e.g. isopropyl-β-d-1-thiogalactopyranoside, lactose, arabinose, maltose, tetracycline, anhydrotetracycline, vavlycin, xylose, copper, zinc, and the like.

In one embodiment, the modified bacterial cells further comprise a nucleic acid sequence encoding a signal peptide operably linked to the exogenous gene, wherein the signal peptide directs cotranslational export of the protein from the cytoplasm to the periplasm. In some embodiments, the signal peptide is derived from the Sec and Tat secretion pathways. In particular embodiments, the signal peptide is derived from DsbA, pelB, OmpA, TolB, MalE, lpp, TorA, or HylA.

In some embodiments, the culture medium has an $OD_{600}$ between about 0.1 to about 500; between about 0.2 to about 100, between about 0.5 to about 10, between about 1 to about 2. In exemplary embodiments, the medium has an $OD_{600}$ of about 1.1.

Expression of the exogenous gene may be induced for about 1 hour to about 1 week; for about 1 hour to about 1 day; for about 1 hour to about 10 hours; for about 10 hours to about 1 week; for about 10 hours to about 1 day; for about 1 day to about 1 week.

The yield of the protein of interest may be about 0.1 g/L medium to about 500 g/L medium; about 1 g/L medium to about 500 g/L medium; about 1 g/L medium to about 100 g/L medium; about 1 g/L medium to about 10 g/L medium; about 10 g/L medium to about 500 g/L medium; about 10 g/L medium to about 100 g/L medium; about 100 g/L medium to about 500 g/L medium. The yield of the protein of interest may be about 10 mg/L medium to about $10^3$ mg/L medium; about 20 mg/L medium to about 500 mg/L medium; about 100 mg/L medium to about 250 mg/L medium; or about 1 mg/L medium to about 10 mg/L medium. The yield of the protein of interest may be increased by at least about 2-fold, 3-fold, 5-fold, 8-fold, 10-fold, as compared to a method of making the protein of interest from genetically identical cells in an unswitched state. The yield of the protein of interest may be increased by from about 2-fold to about 100-fold, from about 2-fold to about 50-fold, from about 5-fold to about 25-fold, or from about 10-fold to about 20-fold. The yield of the protein of interest may be increased by from about 2-fold to about 10-fold, from about 2-fold to about 20-fold, or from about 2-fold to about 30-fold, as compared to a method of making the protein of interest from genetically identical cells in an unswitched state.

In some embodiments, the increased protein yields are increased as compared to methods of making a protein of interest from genetically identical cells under conditions that do not induce a switched L-form (e.g., wherein said conditions that do not induce a switched form are otherwise identical to conditions that provide increased protein of interest). In some cases, the conditions that do not induce a switched L-form comprise the absence of, or an insufficient amount of, one or more antibiotics that inhibit peptidoglycan biogenesis in the cell. In some cases, the conditions that do not induce a switched form additionally or alternatively comprise a magnesium concentration of less than 6 mM, less than 5 mM, less than 4 mM, less than 3 mM, less than 2 mM, or about 1 mM. In some cases, the conditions that do not induce a switched form additionally or alternatively comprise conditions in which the bacterial cell comprises a periplasmic space that is about 5% to about 30% or about 10% to about 20% of total cell volume.

In another aspect, the present invention provides a fermentation vessel containing any one of the foregoing cell cultures, wherein the cell culture contained by the fermentation vessel comprises a volume of medium of about, or of at least about, 1 L; 10 L; 100 L; 250 L; 500 L; or 1,000 L. In some cases, the fermentation vessel is a component of a fermentation system. In some cases, the fermentation system further comprises modules for controlling oxygen, carbon, or pH, or a combination of 2 or 3 thereof.

DETAILED DESCRIPTION

Figure 1:
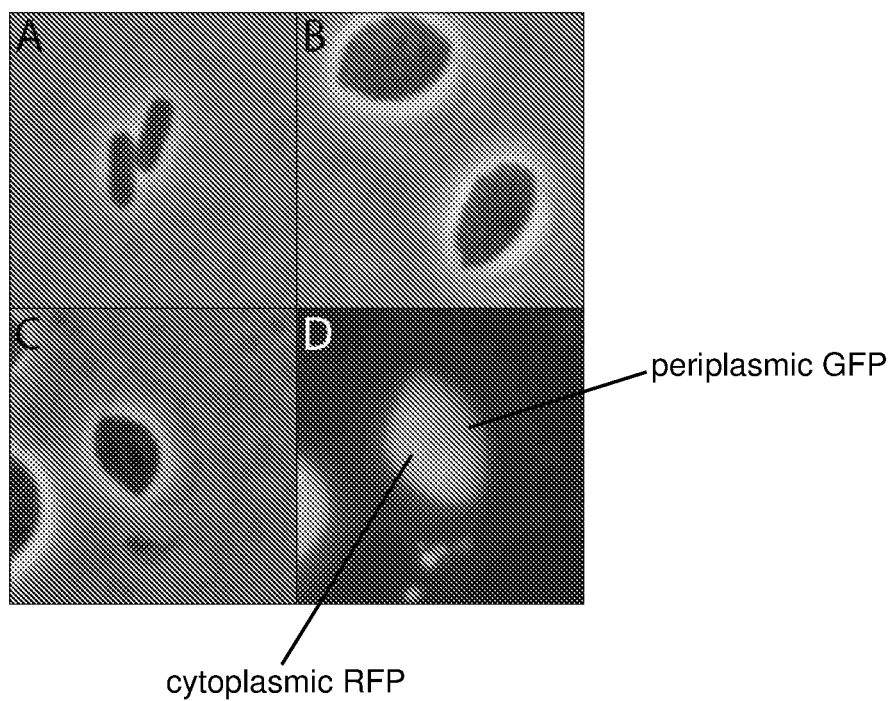
FIG. 1 depicts the physiological state difference between switched and unswitched cells. A) Unswitched *Escherichia coli* cells. B) Same *Escherichia coli* population as figure A but has undergone the physiological switch. C) Phase contrast of switched *Escherichia coli* cell containing cytoplasmic RFP and periplasmic GFP. D) Fluorescent imaging of cell in figure C illustrates targeted protein localization.
Figure 2:
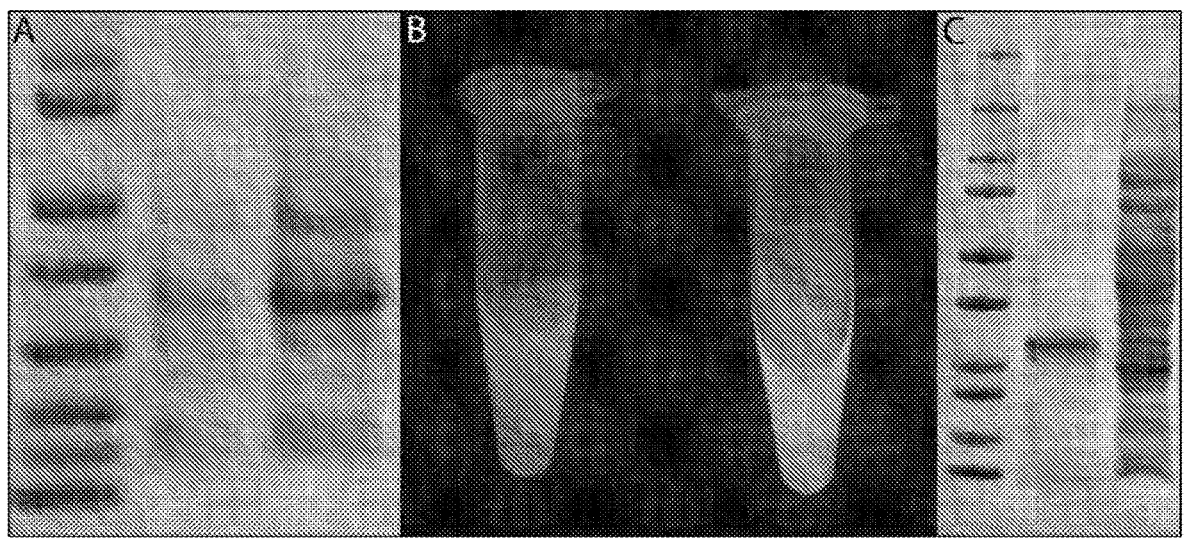
FIG. 2 depicts enhanced protein production in switched cells. A-B) Target protein for T7 inducible protein production is periplasmic expressed GFP, produced in *Escherichia coli* BL21. The same population of cells was used and induced at OD 1.1. A) Protein ladder (lane 1), IPTG induced protein production (lane 2), IPTG induced protein production with physiological switch (lane 3). B) Two vials of the cell GFP induced cultures with IPTG only on left and IPTG+Switch on right. C) Expression of a 22KD collagen using switched cells showing protein ladder (lane 1), supernatent after protein production (lane 2), cell pellet (lane 3).
Figure 3:
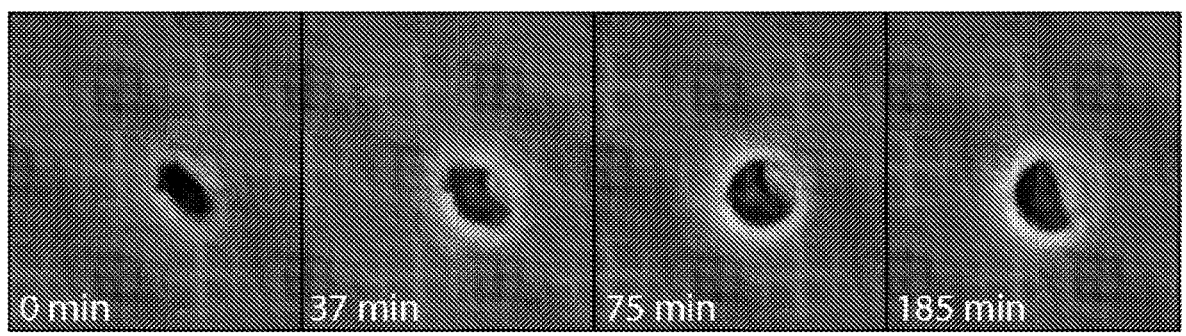
FIG. 3 depicts a timelapse of *Escherichia coli* cell switching over time.
Figure 4:
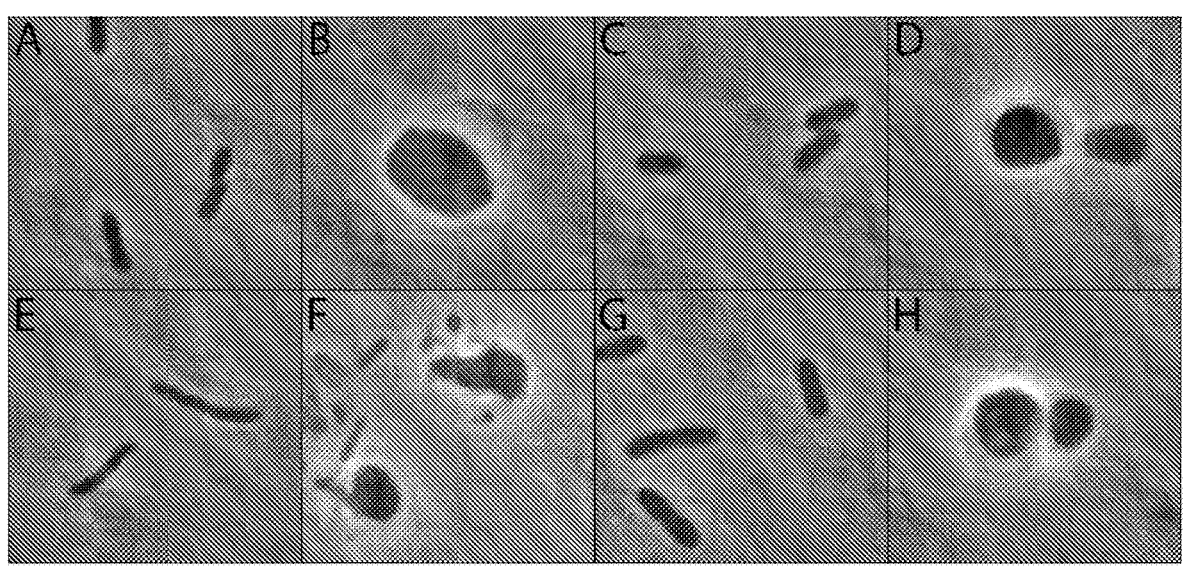
FIG. 4 illustrates other organisms undergoing the physiological switch. A) *Agrobacterium tumefaciens* normal physiology. B) *Agrobacterium tumefaciens* switched physiology. C) *Pseudomonas aeruginosa* PAO1 normal physiology. D) *Pseudomonas aeruginosa* PAO1 switched physiology. E) *Brevundimonas diminuta* normal physiology. F) *Brevundimonas diminuta* switched physiology. G) *Agrobacterium tumefaciens* normal physiology. H) *Agrobacterium tumefaciens* switched physiology.

In the following description, certain specific details are set forth in order to provide a thorough understanding of various embodiments of the disclosure. However, one skilled in the art will understand that the disclosure may be practiced without these details.

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

As used herein the term "about" refers to ±10%.

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this disclosure may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

L-Form Bacteria

The present invention provides a protein production platform comprising modified bacterial cells exhibiting a novel physiological switch phenotype (L-form) which inhibits cell division and promotes the growth of the periplasmic space in comparison to the cytoplasmic space. Recombinant protein production in these cells is dramatically increased compared to that in non-switched cells. This has been tested in several species of Gram negative bacteria (Gammaproteobacteria: *Escherichia coli, Vibrio natriegens*, and *Pseudomonas fluorescens*; and Alphaproteobacteria: *Caulobacter crescentus, Agrobacterium tumefaciens*, and *Brevundimonas diminuta*), which suggest a conserved mechanism that can be applied to all gram-negative recombinant protein production. These cells still contain and inner and outer membrane but lack a functional peptidoglycan cell wall. The cell shape is spherical and increases in volume over time. While the periplasmic space normally comprises only 10-20% of the total cell volume, the periplasmic compartment of the switched state of the subject invention can comprise up to 90% of total cell volume. Remarkably, and unexpectedly, the cells remain viable and are able to undergo metabolic processes and produce recombinant proteins of interest.

The term "recombinant bacterial cell" as used herein refers to a cell that has been engineered to express a target protein.

The term "coccus" as used herein refers to a bacterial cell having a spherical morphology. Generally the longest dimension of a coccus form bacterial cell is no more than 25%, 40%, 50%, or 100% larger than the shortest dimension.

The term "bacillus" as used herein refers to a bacterial cell having a rod-shaped morphology. Typically the longest dimension of a bacillus form bacterial cell is greater than twice the length of the shortest dimension. As such, the longest dimension of a bacillus form bacterial cell can be at least 3, 4, 5, 6, 7, 8, 9, or 10 times the length of the shortest dimension.

The term "periplasmic volume" refers to the total volume contained in the periplasm, which is the region between the outer membrane and the plasma membrane of the bacterial cell.

The term "cytoplasmic volume" refers to the total volume contained in the cytoplasm, which is the region inside the plasma membrane of the bacterial cell.

Target Proteins

The present invention provides a platform of recombinant bacterial cells comprising exogenous genes for producing a protein of interest or "target protein" which is heterologous to the host. A protein or nucleic acid (e.g., nucleic acid encoding a protein, expression cassette, or expression vector) is heterologous to the host if it is not naturally occurring in the host, or is present in the host in a non-naturally occurring context (e.g., a non-natural genomic location or a non-natural subcellular location). For example, a naturally occurring gene can be operably linked to a promoter that is not operably linked to the naturally occurring gene in a corresponding wild-type organism, thereby forming a heterologous expression cassette in a modified bacterial cell. As another example, a naturally occurring genomic fragment that does not naturally exist in a plasmid in a wild-type bacterium can be subcloned into a plasmid and transformed into that bacterium, thereby forming a heterologous plasmid in a modified bacterial cell. The term "exogenous gene" refers to a gene that is introduced into the host organism by gene transfer. In some embodiments, exogenous genes encoding the target proteins of the invention are incorporated into expression vectors, which can be extrachromosomal or designed to integrate into the genome of the host cell into which it is introduced. Expression of the exogenous genes may be constitutive or inducible.

In some embodiments, the exogenous gene (e.g., cDNA or genomic DNA) used to produce the recombinant protein of interest, is suitably inserted into a replicable vector for expression in the bacterium under the control of a suitable promoter for bacteria. Many vectors are available for this purpose, and selection of the appropriate vector will depend mainly on the size of the nucleic acid to be inserted into the vector and the particular host cell to be transformed with the vector. Each vector contains various components depending on its function (amplification of DNA or expression of DNA) and the particular host cell with which it is compatible. Expression vectors can contain any number of appropriate regulatory sequences (including, but not limited to, transcriptional and translational control sequences, promoters, ribosomal binding sites, enhancers, origins of replication, etc.) or other components (selection genes, etc.), all of which are operably linked as is well known in the art.

Expression vectors contain a nucleic acid sequence that enables the vector to replicate in one or more selected host cells. Such sequences are well known for a variety of bacteria. The origin of replication from the plasmid pBR322 is suitable for most Gram-negative bacteria.

Expression vectors also generally contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host cell. Those cells that are successfully transformed with an exogenous gene produce a protein conferring drug resistance and thus survive the selection regimen. In one embodiment, the expression vector selection gene is not a gene that encodes for resistance to an inhibitor of peptidoglycan biogenesis in the bacterial cell.

The expression vector for producing a target protein may also contain an inducible promoter that is recognized by the host bacterial organism and is operably linked to the nucleic acid encoding the target protein. Inducible promoters suitable for use with bacterial hosts include the β-lactamase and lactose promoter systems (Chang et al., Nature, 275:615 (1978); Goeddel et al., Nature, 281:544 (1979)), the arabinose promoter system, including the araBAD promoter (Guzman et al., J. Bacterid., 174: 7716-7728 (1992); Guzman et al., J. Bacterid., 177:4121-4130 (1995); Siegele and Hu, Proc. Natl. Acad. Sci. USA, 94:8168-8172 (1997)), the rhamnose promoter (Haldimann et al., J. Bacterid., 180: 1277-1286 (1998)), the alkaline phosphatase promoter, a tryptophan (trp) promoter system (Goeddel, Nucleic Acids Res., 8:4057 (1980) and EP 36,776), the $P_{LtetO\text{-}1}$ and $P_{lac/}$ ara-1 promoters (Lutz and Bujard, Nucleic Acids Res., 25:1203-1210 (1997)), and hybrid promoters such as the tac promoter. deBoer et al., Proc. Natl. Acad. Sci. USA, 80:21-25 (1983). However, other known bacterial inducible promoters and low-basal-expression promoters are suitable. Their nucleotide sequences have been published, thereby enabling a skilled worker operably to ligate them to DNA encoding the target protein.

Promoters for use in bacterial systems may also contain a Shine-Dalgarno (SD) sequence operably linked to the DNA encoding the target protein. The promoter can be removed from the bacterial source DNA by restriction enzyme digestion and inserted into the vector containing the desired DNA.

Construction of suitable vectors containing one or more of the above-listed components employs standard ligation techniques commonly known to those of skill in the art. Isolated plasmids or DNA fragments are cleaved, tailored, and re-ligated in the form desired to generate the plasmids required. Instructions for handling DNA, digestion and ligation of DNA, transformation and selection of transformants can be found inter alfa in the known manual by Sambrook et al. "Molecular Cloning: A Laboratory Manual, Second Edition (Cold Spring Harbor Laboratory Press, 1989).

The term "gene" as used herein refers to a nucleic acid fragment that expresses a specific protein, and which may refer to the coding region alone or may include regulatory sequences preceding (5' non-coding sequences) and following (3' non-coding sequences) the coding sequence.

The term "expression vector" refers to an assembly which is capable of directing the expression of the exogenous gene. The expression vector may include a promoter which is operably linked to the exogenous gene.

The term "constitutive" as used herein refers to an exogenous gene that is expressed and not known to be subject to regulation that completely causes cessation of expression under most environmental and developmental conditions.

The term "inducible" as used herein refers to an exogenous gene that is expressed in response to presence of an inducer such as an exogenous chemical, heat, or light. Standard procedures may be followed to induce protein production in the L-form bacterial cells described herein. In some embodiments, the strain BL21(DE3) containing the plasmid pET28a may be used to drive the IPTG/lactose inducible production of recombinant proteins.

The term "target protein" as used herein refers generally to peptides and proteins having more than about 10 amino acids. The target proteins are preferably mammalian proteins. Target proteins generally exclude fluourescent proteins. In some embodiments the target protein is other than mCherry. In some embodiments the target protein is other than green fluorescent protein (GFP).

The term "therapeutic protein" as used herein refers to those proteins that have demonstrated biological activity and may be employed to treat a disease or disorder by delivery to a patient in need thereof by an acceptable route of administration. The biological activity of therapeutic proteins may be demonstrated in vitro or in vivo and results from interaction of the protein with receptors and/or other intracellular or extracellular components leading to a biological effect. Example of therapeutic proteins include, but are not limited to, molecules such as, e.g., renin, a growth hormone, including human growth hormone; bovine growth hormone; growth hormone releasing factor; parathyroid hormone; thyroid stimulating hormone; lipoproteins; al-antitrypsin; insulin A-chain; insulin B-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha; tumor necrosis factor-beta; enkephalinase; a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF-$\beta$; cardiotrophins (cardiac hypertrophy factor) such as cardiotrophin-1 (CT-1); platelet-derived growth factor (PDGF); fibroblast growth factor such as aFGF and bFGF; epidermal growth factor (EGF); transforming growth factor (TGF) such as TGF-alpha and TGF-beta, including TGF-$\beta$1, TGF-$\beta$2, TGF-$\beta$3, TGF-$\beta$4, or TGF-$\beta$5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-13; anti-HER-2 antibody; superoxide dismutase; T-cell receptors; surface membrane proteins; decay accelerating factor; viral antigen such as, for example, a portion of the AIDS envelope; transport proteins; homing receptors; addressins; and regulatory proteins.

In some embodiments the target protein is an antibody. Antibodies produced by the claimed invention may be monoclonal antibodies that are homogeneous populations of antibodies to a particular antigenic determinant (e g., a cancer cell antigen, a viral antigen, a microbial antigen, a protein, a peptide, a carbohydrate, a chemical, nucleic acid, or fragments thereof). Such antibodies may be of any immunoglobulin class including IgG, IgM, IgE, IgA, and IgD and any subclass thereof.

Useful monoclonal antibodies include, but are not limited to, human monoclonal antibodies, humanized monoclonal antibodies, antibody fragments, or chimeric human-mouse (or other species) monoclonal antibodies.

The antibody can also be a bispecific antibody. Bispecific antibodies may have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (WO 94/04690; Suresh et al. (1986) Methods in Enzymology, 121:210; Rodrigues et al. (1993) J. of Immunology 151:6954-6961; Carter et al. (1992) Bio/ Technology 10:163-167; Carter et al. (1995) J. of Hematotherapy 4:463-470; Merchant et al. (1998) Nature Biotechnology 16:677-681.

The antibody, as defined, can be a functionally active fragment, derivative or analog of an antibody that immuno-specifically binds to cancer cell antigens, viral antigens, or microbial antigens or other antibodies bound to tumor cells or matrix. In this regard, "functionally active" means that the fragment, derivative or analog is able to elicit anti-anti-idiotype antibodies that recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art, e.g. the BIA core assay (Kabat et al. (1991) in Sequences of Proteins of Immunological Interest, Fifth Edition, National Institute of Health, Bethesda, Md.; Kabat et al. (1980) J. of Immunology 125(3):961-969).

Other useful antibodies include fragments of antibodies such as, but not limited to, F(ab')2 fragments, which contain the variable region, the light chain constant region and the CH1 domain of the heavy chain, can be produced by pepsin digestion of the antibody molecule, and Fab fragments, which can be generated by reducing the disulfide bridges of the F(ab')2 fragments. Other useful antibodies are heavy chain and light chain dimers of antibodies, or any minimal fragment thereof such as Fvs or single chain antibodies (SCAs) (e.g., as described in U.S. Pat. No. 4,946,778; Bird (1988) Science 242:423-42; Huston et al., (1988) Proc. Natl. Acad. Sci. U.S.A. 85:5879-5883; and Ward et al. (1989) Nature 334:544-54), or any other molecule with the same specificity as the antibody.

The antibody may be a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, such as at least 10, 20 or 50 amino acid portion of the protein) that is not the antibody. The antibody or fragment thereof may be covalently linked to the other protein at the N-terminus of the constant domain.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. (1984) Proc. Natl. Acad. Sci. U.S.A., 81:6851-6855). A chimeric antibody is a molecule in which different portions are derived from different animal species, such as those having a variable region derived from murine monoclonal and human immunoglobulin constant regions (U.S. Pat. Nos. 4,816,567; 4,816,397). Chimeric antibodies include "primatized" antibodies comprising variable domain antigen-binding sequences derived from a non-human primate (e.g., Old World Monkey, Ape etc.) and human constant region sequences.

Therapeutic monoclonal antibodies that may be produced by the bacteria and methods of the invention include, but are not limited to, trastuzumab (HERCEPTIN®, Genentech, Inc., Carter et al. (1992) Proc. Natl. Acad. Sci. U.S.A., 89:4285-4289; U.S. Pat. No. 5,725,856); anti-CD20 antibodies such as chimeric anti-CD20 "C2B8" (U.S. Pat. No. 5,736,137); rituximab (RITUXAN®), ocrelizumab, a chimeric or humanized variant of the 2H7 antibody (U.S. Pat. No. 5,721,108; WO 04/056312) or tositumomab (BEXXAR®); anti-IL-8 (St John et al. (1993) Chest, 103: 932, and WO 95/23865); antibodies targeting other interleukins, such as IL-1, IL-2, IL-3, IL-4, IL-5, IL-6, IL-7, IL-9, IL-10, IL-12, and IL-13; anti-VEGF antibodies including humanized and/or affinity matured anti-VEGF antibodies such as the humanized anti-VEGF antibody huA4.6.1 bevacizumab (AVASTIN®, Genentech, Inc., Kim et al. (1992) Growth Factors 7:53-64; WO 96/30046; WO 98/45331); anti-PSCA antibodies (WO 01/40309); anti-CD40 antibodies, including S2C6 and humanized variants thereof (WO 00/75348); anti-CD11a (U.S. Pat. No. 5,622,700; WO 98/23761; Steppe et al. (1991) Transplant Intl. 4:3-7; Hourmant et al. (1994) Transplantation 58:377-380); anti-IgE (Presta et al. (1993) J. Immunol. 151:2623-2632; WO 95/19181); anti-CD18 (U.S. Pat. No. 5,622,700; WO 97/26912); anti-IgE, including E25, E26, and E27 (U.S. Pat. Nos. 5,714,338 and 5,091,313; WO 93/04173; U.S. Pat. No. 5,714,338); anti-Apo-2 receptor antibody (WO 98/51793); anti-TNF-alpha antibodies including cA2 (REMICADE®), CDP571, and MAK-195 (U.S. Pat. No. 5,672,347; Lorenz et al. (1996) J. Immunol. 156(4): 1646-1653; Dhainaut et al. (1995) Crit. Care Med. 23(9):1461-1469); anti-Tissue Factor (TF) (EP 0 420 937 B1); anti-human alpha-4 beta 7 integrin (WO 98/06248); anti-EGFR, chimerized or humanized 225 antibody (WO 96/40210); anti-CD3 antibodies such as OKT3 (U.S. Pat. No. 4,515,893); anti-CD25 or anti-tac antibodies such as CHI-621 SIMULECT® and ZENAPAX® (U.S. Pat. No. 5,693,762); anti-CD4 antibodies such as the cM-7412 antibody (Choy et al. (1996) Arthritis Rheum 39(1):52-56); anti-CD52 antibodies such as CAMPATH-1H (Riechmann et al. (1988) Nature 332: 323-337); anti-Fc receptor antibodies such as the M22 antibody directed against Fc gamma RI as in Graziano et al. (1995) J. Immunol. 155(10):4996-5002; anti-carcinoembryonic antigen (CEA) antibodies such as hMN-14 (Sharkey et al. (1995) Cancer Res. 55(23 Suppl): 5935s-5945s; antibodies directed against breast epithelial cells including huBrE-3, hu-Mc 3 and CHL6 (Ceriani et al. (1995) Cancer Res. 55(23):5852s-5856s; and Richman et al. (1995) Cancer Res. 55(23 Supp):5916s-5920s); antibodies that bind to colon carcinoma cells such as C242 (Litton et al. (1996) Eur J. Immunol. 26(1):1-9); anti-CD38 antibodies, e.g., AT 13/5 (Ellis et al. (1995) J. Immunol. 155(2):925-937); anti-CD33 antibodies such as Hu M195 (Jurcic et al. (1995) Cancer Res 55(23 Suppl):5908s-5910s) and CMA-676 or CDP771; anti-CD22 antibodies such as LL2 or LymphoCide (Juweid et al. (1995) Cancer Res 55(23 Suppl):5899s-5907s); anti-EpCAM antibodies such as 17-1A (PANOREX®); anti-GpIIb/IIIa antibodies such as abciximab or c7E3 Fab (REOPRO®); anti-RSV antibodies such as MEDI-493 (SYNAGIS®); anti-CMV antibodies such as PROTOVIR®); anti-HIV antibodies such as PRO542; anti-hepatitis antibodies such as the anti-Hep B antibody OSTAVIR®); anti-CA 125 antibody OvaRex; anti-idiotypic GD3 epitope antibody BEC2; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID10 and the anti-HLA DR antibody Oncolym (Lym-1).

In some embodiments the target protein is non-therapeutic protein. Non-therapeutic proteins include, but are not limited to collagen and derivatives thereof, albumin, ovalbumin, rennet, fibrin, casein (including αS1, αS2, β, κ), elastin, keratin, myosin, fibronectin, laminin, nidogen-1, vitronectin, silk fibroins, prolyl hydroxylases, lysyl hydroxylases, glycosyltransferases, hemeproteins and any other structural proteins and enzymes of commercial and/or academic interest.

In some embodiments the target protein is collagen. The term "collagen" as used herein refers to the main protein of connective tissue that has a high tensile strength and that has been found in most multicellular organisms. Collagen is a major fibrous protein, and it is also the nonfibrillar protein in basement membranes. It contains an abundance of glycine, proline, hydroxyproline, and hydroxylysine. Currently, collagen types I-XIX have been identified and they differ by the amino acid structure of the alpha chain. The term "collagen" as used herein is understood as meaning all collagen types and any form of collagen, whether native nor not, atelocollagen, insoluble collagen, collagen fibers, soluble collagen, and acid-soluble collagen.

Growth Media

Growth media suitable for culturing the L-form bacteria described herein comprise at least 4 mM magnesium, preferably greater than 4 mM, more preferably greater than 5 mM, and still more preferably greater than 6 mM magnesium concentration, which may be in the form of either magnesium sulfate ($MgSO_4$), magnesium chloride ($MgCl_2$), or other magnesium salts known in the art. The media may also contain an osmotic stabilizer such as sucrose, glucose, or a betaine. In some embodiments, the concentration of osmotic stabilizer should be at least about 3%, 4% or 5% weight/volume.

The term "osmotic stabilizer" as used herein refers to a component used to control the osmotic strength of the medium and reduce turgor pressure inside the bacterial cells. Osmotic stabilizers can include, but are not limited to, e.g. sugars (e.g., arabinose, glucose, sucrose, glycerol, sorbitol, mannitol, fructose, galactose, saccharose, maltotrioseerythritol, ribitol, pentaerythritol, arabitol, galactitol, xylitol, iditol, maltotriose, and the like), betaines (e.g., trimethylglycine), proline, one or more salts such as an ammonium, potassium, or sodium salt (e.g., sodium chloride), one or more polymers (e.g., polyethylene glycol, polyethylene glycol monomethylether, polysucrose, polyvinylpyrrolidone, polypropylene glycol), or a combination thereof. In some cases, the concentration of the osmotic stabilizer(s) in the medium is at least about 4%, 5%, 6%, or 7% (w/v). In further embodiments, the concentration of osmotic stabilizer is at least about 8%, 9%, or 10% (w/v). In some embodiments, the concentration of the osmotic stabilizer in the medium is between about 5% to about 20% (w/v).

In some embodiments, the total concentration of osmotic stabilizer (e.g., one or more of the osmotic stabilizers described above) is sufficient to provide a culture medium having an osmolality equal to the osmolality of switch media 1, switch media 2, or bioreactor media MGZ12, described hereinbelow in Example 1. In some embodiments, the the total concentration of osmotic stabilizer (e.g., one or more of the osmotic stabilizers described above) is sufficient to provide a culture medium having an osmolality that is from about 50% lower to about 50% higher than the osmolality of switch media 1, switch media 2, or bioreactor media MGZ12, described hereinbelow in Example 1. In some embodiments, the the total concentration of osmotic stabilizer (e.g., one or more of the osmotic stabilizers described above) is sufficient to provide a culture medium having an osmolality that is from about 25% lower to about 25% higher, or from about 10% lower to about 10% higher than the osmolality of switch media 1, switch media 2, or bioreactor media MGZ12, described hereinbelow in Example 1.

The term "sugar" as used herein refers to reducing sugars (e.g., cellobiose, fructose, galactose, glucose, glyceraldehyde, lactose, maltose, and ribose), non-reducing sugars (e.g., melezitose, melibiose, raffinose, sorbose, sucralose, sucrose, trehalose, and verbascose), and sugar alcohols (e.g., amltitol, arabitol, dulcitol, erythritol, glycerol, glycol, iditol, isomalt, lactitol, mannitol, rebitol, sorbitol, threitol, and xylitol)

The term "betaine" as used herein refers to fully N-methylated amino acids, including, but not limited to trimethylglycine.

Salts and other nutrients should be added to the media to supplement growth. Salts and media compositions that support the physiological switch physiology that have been tested are M63 salt media, M9 salt media, PYE media, and Luria-Bertani (LB) media. Any necessary supplements besides carbon, nitrogen, and inorganic phosphate sources may also be included at appropriate concentrations introduced alone or as a mixture with another supplement or medium such as a complex nitrogen source. In certain embodiments, the medium further comprises one or more ingredients selected from: ammonium chloride, ammonium sulfate, calcium chloride, casamino acids, iron(II) sulfate, magnesium sulfate, peptone, potassium phosphate, sodium chloride, sodium phosphate, and yeast extract.

In some embodiments, the cell culture is free of animal-derived components. In some embodiments, the cell culture comprises a defined medium. In some embodiments, the cell culture is free of yeast extract.

In some embodiments, the cell culture comprises from about $1 \times 10^8$ bacterial cells per mL of culture volume to about $1 \times 10^{10}$ bacterial cells per mL in a volume of at least about 1 L (e.g., from about 1 L to about 500,000 L, from about 1 L to about 10,000 L, from about 1 L to about 1,000 L, from about about 1 L to about 500 L, or from about 1 L to about 250 L). In some embodiments, the cell culture comprises from about $4 \times 10^8$ bacterial cells per mL of culture volume to about $1 \times 10^9$ bacterial cells per mL in a volume of at least about 1 L (e.g., from about 1 L to about 500,000 L, from about 1 L to about 10,000 L, from about 1 L to about 1,000 L, from about about 1 L to about 500 L, or from about 1 L to about 250 L).

In certain embodiments, the medium also contains a selection agent, chosen based on the construction of the expression vector, to selectively permit growth of prokaryotic cells containing the expression vector. For example, kanamycin is added to media for growth of cells expressing a kanamycin resistant gene.

In some embodiments, the cell culture comprises at least one exogenous antibiotic inhibitor of bacterial cell peptidoglycan biogenesis. An exogenous antibiotic inhibitor is an antibiotic as is commonly understood in the art and includes antimicrobial agents naturally produced by microorganisms such as bacteria (including *Bacillus* species), actinomycetes (including *Streptomyces*) or fungi that inhibit growth of or destroy other microbes, or genetically-engineered thereof and isolated from such natural source. Substances of similar structure and mode of action can be synthesized chemically, or natural compounds can be modified to produce semi-synthetic antibiotics. Exemplary classes of antibiotics include, but are not limited to, (1) β-lactams, including the penicillins, cephalosporins monobactams, methicillin, and carbapenems; (2) aminoglycosides, e.g., gentamicin, kanamycin, neomycin, tobramycin, netilmycin, paromomycin, and amikacin; (3) tetracyclines, e.g., doxycycline, minocycline, oxytetracycline, tetracycline, and demeclocycline; (4) sulfonamides (e.g., mafenide, sulfacetamide, sulfadiazine and sulfasalazine) and trimethoprim; (5) quinolones, e.g., ciprofloxacin, norfloxacin, and ofloxacin; (6) glycopeptides (e.g., vancomycin, telavancin, teicoplanin); (7) macrolides, which include for example, erythromycin, azithromycin, and clarithromycin; (8) carbapenems (e.g., ertapenem, doripenem, meropenem, and imipenem); (9) cephalosporins (e.g., cefadroxil, cefepime, and ceftobiprole); (10) lincosamides (e.g., clindamycin, and lincomycin); (11) monobactams (e.g., aztreonam); (12) nitrofurans (e.g., furazolidone, and nitrofurantoin); (13) Penicillins (e.g., amoxicillin, and Penicillin G); (14) polypeptides (e.g., bacitracin, colistin, and polymyxin B); and (15) other antibiotics, e.g., ansamycins, polymycins, carbacephem, chloramphenicol, lipopeptide, and drugs against mycobacteria (e.g., the ones causing diseases in mammals, including tuberculosis (*Mycobacterium tuberculosis*) and leprosy (*Mycobacterium leprae*), and any combinations thereof. An exogenous antibiotic inhibitor of bacterial cell peptidoglycan biogenesis can be used, present in, or added to a culture, in an amount or concentration effective to inhibit or block bacterial cell peptidoglycan biogenesis. An exogenous antibiotic inhibitor of bacterial cell peptidoglycan biogenesis can be used, present in, or added to a culture, in an amount effective to inhibit or block bacterial cell division. An exogenous antibiotic inhibitor of bacterial cell peptidoglycan biogenesis can be used, present in, or added to a culture, in an amount or concentration effective to kill a bacterial cell in a culture medium containing less than 6, 5, 4, 3, or about 1 mM magnesium and/or osmotic stabilizers. An exogenous antibiotic inhibitor of bacterial cell peptidoglycan biogenesis can be used, present in, or added to a culture, in an amount or concentration that is at or above a minimum inhibitory concentration of the antibiotic inhibitor in control medium that does not induce a switched form. An exogenous antibiotic inhibitor of bacterial cell peptidoglycan biogenesis can be used, present in, or added to a culture, in an amount or concentration that is effective to reduce colony formation of bacteria on a test plate (e.g., LB agar) by at least about 95% or 99% as compared to the absence of the exogenous antibiotic inhibitor in a control test plate.

In some embodiments, the cell culture comprises at least two structurally distinct exogenous antibiotic inhibitors of bacterial cell peptidoglycan biogenesis. In some cases, the at least two structurally distinct exogenous antibiotic inhibitors of bacterial cell peptidoglycan biogenesis inhibit different components of a peptidoglycan biogenesis pathway in the bacterial cell (e.g., the at least two structurally distinct exogenous antibiotic inhibitors inhibit different enzymes of the peptidoglycan biogenesis pathway in the bacterial cell). In some cases, the cell culture comprises an exogenous antibiotic inhibitor of a transglycosylase component of bacterial cell peptidoglycan biogenesis. In some cases, the cell culture comprises an exogenous antibiotic inhibitor of a transpeptidase component of bacterial cell peptidoglycan biogenesis. In some cases, the cell culture comprises an exogenous antibiotic inhibitor of UDP-N-acetylmuramyl (UDP-MurNAc)-pentapeptide biogenesis or UDP-N-acetylglucosamine (UDP-GlcNAc) biogenesis.

In some cases, the cell culture comprises an exogenous antibiotic inhibitor of MurA, MurB, MurC, MurD, MurE, MurF, MraY, MurG, FemX, FemA, FemB, FtsW, or a penicillin binding protein (PBP). In some cases, the cell culture comprises at least two structurally distinct exogenous antibiotic inhibitors, wherein the at least two structurally distinct exogenous antibiotic inhibitors inhibit different proteins selected from MurA, MurB, MurC, MurD, MurE, MurF, MraY, MurG, FemX, FemA, FemB, FtsW, or a penicillin binding protein (PBP). In some embodiments, the cell culture comprises at least one or at least two structurally distinct antibiotic(s) selected from: β-lactam antibiotics, phosphonic acid antibiotics, polypeptide antibiotics, D-cycloserine, and glycopeptide antibiotics, wherein the antibiotic(s) inhibit peptidoglycan biogenesis in the bacterial cell.

In some embodiments, the culture medium comprises at least one reactive oxygen species (ROS) scavenger (e.g., reduced glutathione (GSH), or a thiol containing non-peptidic small molecule having a molecular weight from about 70 g/mol to about 350 g/mol, or from about 75 g/mol to about 155 g/mol).

In some embodiments, the culture medium comprises an antibiotic (e.g., second or third antibiotic) that selects for the presence of a selectable marker in an expression vector that comprises an exogenous gene encoding for a protein of interest. In some embodiments, the antibiotic that selects for the presence of a selectable marker in the expression vector is not an inhibitor of peptidoglycan biogenesis in the bacterial cell.

Physiological Switch

Without being bound by theory, the cell morphology that promotes recombinant protein production and inhibits cell division appears to be driven by the removal of the cell wall under the media conditions stated above. In some embodiments, the methods for removal/inhibition of cell wall synthesis can be through the use of antibiotics that inhibit peptidoglycan synthesis (such as ampicillin, carbenicillin, penicillins or fosfomycin), or other methods known in the art.

In some embodiments, the antibiotic is selected from: β-lactam antibiotics, phosphonic acid antibiotics, polypeptide antibiotics, and glycopeptide antibiotics. In some embodiments, the antibiotic is an antibiotic selected from: penicllins, cephalosporins, carbapenems, and monobactams. In some embodiments, the antibiotic is selected from: alafosfalin, amoxicillin, ampicillin, aztreonam, bacitracin, carbenicillin, cefamandole, cefotaxime, cefsulodin, cephalothin, fosmidomycin, methicillin, nafcillin, oxacillin, penicillin g, penicillin v, fosfomycin, primaxin, D-cycloserine, and vancomycin.

Periplasmic Targeting

When having an appropriate signal sequence, recombinantly produced polypeptides can be secreted into the periplasmic space of bacterial cells. Joly, J. C. and Laird, M. W., in The Periplasm ed. Ehrmann, M., ASM Press, Washington D.C., (2007) 345-360. In the chemically oxidizing environment of the periplasm the formation of disulfide bonds and thereby the functionally correct folding of polypeptides is favored.

In general, the signal sequence may be a component of the expression vector, or it may be a part of the exogenous gene that is inserted into the vector. The signal sequence selected should be one that is recognized and processed (i.e., cleaved by a signal peptidase) by the host cell. For bacterial host cells that do not recognize and process the native signal sequence of the exogenous gene, the signal sequence is substituted by any commonly known bacterial signal sequence.

In some embodiments, recombinantly produced polypeptides can be targeted to the periplasmic space using the DsbA signal sequence. Dinh and Bernhardt, J Bacteriol, September 2011, 4984-4987. In some embodiments, recombinantly produced polypeptides can be targeted to the periplasmic space using an DsbA, pelB, OmpA, TolB, MalE, lpp, TorA, or HylA signal sequence. In some embodiments, recombinantly produced polypeptides can be targeted to the periplasmic space using a portion (at least 10%, 25%, 50%, 75%, 95%, 99%) of a gene encoding a protein that is secreted into the periplasmic space. For example, in some embodiments, recombinantly produced polypeptides can be targeted to the periplasmic space using a portion (at least 10%, 25%, 50%, 75%, 95%, 99%) of a gene encoding a protein DsbA, pelB, OmpA, TolB, MalE, lpp, TorA, or HylA, wherein the portion contains the signal sequence of DsbA, pelB, OmpA, TolB, MalE, lpp, TorA, or HylA respectively. In some embodiments, a recombinantly produced polypeptide can be targeted to the periplasmic space by fusing the gene encoding the polypeptide to a nucleic acid encoding all or substantially all of a protein that is secreted into the periplasmic space, e.g., a protein selected from DsbA, pelB, OmpA, TolB, MalE, lpp, TorA, or HylA, thereby producing a fusion protein. Generally, such periplasmic targeting employs an N-terminal fusion in which the signal sequence or portion containing the signal sequence is N-terminal to the polypeptide of interest.

Fermentative Protein Production

The present invention furthermore provides a process for fermentative preparation of a protein, comprising the steps of:
a) culturing a recombinant Gram-negative bacterial cell in a medium comprising a magnesium salt, wherein the concentration of magnesium ions in the medium is at least about 6 mM, and wherein the bacterial cell comprises an exogenous gene encoding the protein, provided that the protein is other than mCherry or green fluorescent protein;
b) inhibiting peptidoglycan biogenesis in the bacterial cell (e.g., by adding to the medium 1, 2, or more antibiotics that inhibit peptidoglycan biogenesis); and
c) harvesting the protein from the medium.

The bacteria may be cultured continuously—as described, for example, in WO 05/021772—or discontinuously in a batch process (batch cultivation) or in a fed-batch or repeated fed-batch process for the purpose of producing the target protein. In some embodiments, protein production is conducted on a large-scale. Various large-scale fermentation procedures are available for production of recombinant proteins. Large-scale fermentations have at least 1,000 liters of capacity, preferably about 1,000 to 100,000 liters of capacity. These fermentors use agitator impellers to distribute oxygen and nutrients, especially glucose (the preferred carbon/energy source). Small-scale fermentation refers generally to fermentation in a fermentor that is no more than approximately 20 liters in volumetric capacity.

For accumulation of the target protein, the host cell is cultured under conditions sufficient for accumulation of the target protein. Such conditions include, e.g., temperature, nutrient, and cell-density conditions that permit protein expression and accumulation by the cell. Moreover, such conditions are those under which the cell can perform basic cellular functions of transcription, translation, and passage of proteins from one cellular compartment to another for the secreted proteins, as are known to those skilled in the art.

The bacterial cells are cultured at suitable temperatures. For E. coli growth, for example, the typical temperature ranges from about 20° C. to about 39° C. In one embodiment, the temperature is from about 25° C. to about 37° C. In another embodiment, the temperature is at about 30° C.

The pH of the culture medium may be any pH from about 5-9, depending mainly on the host organism. For E. coli, the pH is from about 6.8 to about 7.4, or about 7.0.

For induction, typically the cells are cultured until a certain optical density is achieved, e.g., an $OD_{600}$ of about 1.1, at which point induction is initiated (e.g., by addition of an inducer, by depletion of a repressor, suppressor, or medium component, etc.) to induce expression of the exogenous gene encoding the target protein.

After product accumulation, the cells can be vigorously stirred or mixed (e.g., vortexed), and/or centrifuged in order to induce lysis and release of recombinant proteins. The majority of the proteins are typically found in the supernant but any remaining membrane bound proteins can be released using detergants (e.g., a non-ionic detergent such as triton X-100).

In a subsequent step, the target protein, as a soluble or insoluble product released from the cellular matrix, is recovered in a manner that minimizes co-recovery of cellular debris with the product. The recovery may be done by any means, but in one embodiment, can comprise of histidine tag purification through a nickel colum. See for example, Purification of Proteins Using Polyhistidine Affinity Tags, Methods Enzymology. 2000; 326: 245-254.

The target protein captured in the initial recovery step may then be further purified for example by chromatography. General chromatographic methods and their use are known to a person skilled in the art. See for example, Chromatography, 5th edition, Part A: Fundamentals and Techniques, Heftmann, E (ed), Elsevier Science Publishing Company, New York, (1992); Advanced Chromatographic and Electromigration Methods in Biosciences, Deyl, Z. (ed.), Elsevier Science BV, Amsterdam, The Netherlands, (1998); Chromatography Today, Poole, C. F., and Poole, S. K., Elsevier Science Publishing Company, New York, (1991); Scopes, Protein Purification Principles and Practice (1982); Sambrook, J., et al. (ed), Molecular Cloning: A Laboratory Manual, Second Edition, Cold Spring Harbor Laboratory Press, Cold Spring Harbor, N.Y., 1989; or Current Protocols in Molecular Biology, Ausubel, F. M., et al. (eds), John Wiley & Sons, Inc., New York. The following procedures are exemplary of suitable purification procedures: fractionation on immunoaffinity or ion-exchange columns; ethanol precipitation; reversed-phase HPLC; chromatography on silica or on a cation-exchange resin such as DEAE; chromatofocusing; SDS-PAGE; ammonium sulfate precipitation; and gel filtration using, for example, SEPHADEX™ G-75.

The following examples are provided for purposes of illustration, not limitation.

EXAMPLES

Example 1

Construction of the Modified Bacteria

Materials and Methods:
Strains:
Tested Physiological Switch and Protein Production:
E. coli BL21(DE3)—From NEB, product #c2527
E. coli K12 NCM3722—From The Coli Genetic Stock Center, CGSC #12355
Tested Physiological Switch:
Gammaproteobacteria:
Vibrio natriegens—From ATCC, product #14048
Pseudomonas fluorescens—From ATCC, product #31948

*Pseudomonas aeruginosa* PAO1—From ATCC, product #BAA-47
Alphaproteobacteria:
*Caulobacter crescentus*—From ATCC, product #19089
*Agrobacterium tumefaciens/Rhizobium radiobacter*—From ATCC, product #33970
*Brevundimonas diminuta*—From ATCC, product #13184
Media Compositions:
1 Liter 5× m63 Salts:
10 g (NH4)2SO4—From P212121, product #7783-20-2
68 g KH2PO4—From P212121, product #7778-77-0
2.5 mg FeSO4.7H2O—From Sigma Aldrich, product #F7002
Bring volume up to 1 liter with milliQ water
Adjust to pH 7 with KOH (From P212121, product #1310-58-3)
Autoclave mixture
1 Liter of 1M MgSO4:
246.5 g MgSO4 7H2O—From P212121, product #10034-99-8
Bring volume up to 1 liter with milliQ water
Autoclave mixture
1 Liter of Switch Media 1:
133.4 mL 5× m63 Salts
10 mL 1M MgSO4
38.6 g Glucose—From P212121, product #50-99-7
66.6 g Sucrose—From P212121, product #57-50-1
8.33 g LB mix—From P212121, product #lb-miller
Bring volume up to 1 liter with milliQ water
Filter sterilize mixture through a 0.22 µM pore vacuum filter (From Sigma Aldrich, product #CLS430517)
1 Liter of Switch Media 2:
133.4 mL 5× m63 Salts
10 mL 1M MgSO4
38.6 g Glucose—From P212121, product #50-99-7
66.6 g Sucrose—From P212121, product #57-50-1
10 g Yeast Extract—From FisherSci.com, product #J60287A1
Bring volume up to 1 liter with milliQ water
Filter sterilize mixture through a 0.22 µM pore vacuum filter (From Sigma Aldrich, product #CLS430517)
For Bioreactor Growth:
5 liter of bioreactor media MGZ12:
1) Autoclave 1 L of Glucose at concentration of 500 g/L in DI water. From VWR, product #97061-170.
2) Autoclave 1 L of Sucrose at concentration of 500 g/L in DI water. From Geneseesci.com, product #62-112.
3) Autoclave in 3946 mL of DI water:
20 g (NH4)2HPO4. From VWR, product #97061-932.
66.5 g KH2PO4. From VWR, product #97062-348.
22.5 g H3C6H5O7. From VWR, product #BDH9228-2.5KG.
2.95 g MgSO4.7H2O. From VWR, product #97062-134.
10 mL Trace Metals (Teknova), 1000×. From Teknova, product #T1001.
After autoclaving add 400 mL of (1) to (3), 65 mL of 10M NaOH (from VWR, product #97064-480) to (3), and 666 mL of (2) to (3).
A feed of 500 g/L of glucose can be used during fermentation run as needed.
At induction add:
50 mL of 1M MgSO4.7H2O to a 5 L bioreactor
1 to 10 mM concentration of IPTG. From carbosynth.com, product #EI05931
Add Fosfomycin (50 µg/mL or higher) and Carbenicillin (100 µg/mL or higher).

Physiological Switch:
The physiological switch is optimally flipped at an OD 600 of 1 to 1.1 for *E. coli* for growth in shake flasks at volumes up to 1 L. For the other species tested, cultures were grown in switch media and subcultured once cultures reached maximal OD 600. In all cases the physiological switch is flipped through the addition of 100-200 ug/mL Carbenicillin (From P212121, product #4800-94-6) and 50-100 ug/mL Fosfomycin (From P212121, product #26016-99-9). The majority of the population is in the switched state within a few hours. To confirm that cells underwent a physiological switch, cells were imaged on a Nikon Ti-E with perfect focus system, Nikon CFI60 Plan Apo 100× NA 1.45 objective, Prior automated filter wheels and stage, LED-CFP/YFP/mCherry and LED-DA/FI/TX filter sets (Semrock), a Lumencor Sola II SE LED illumination system, and a Hamamatsu Flash 4.0 V2 CMOS camera.

Image Analysis of Physiological Switch:
Images were analyzed using ImageJ to measure dimensions. In the switched state, the spherical outline of the outer membrane is treated as a sphere to calculate total volume ($V=(4/3)\pi r^3$). The cytoplasmic volume is calculated as an ellipsoid that exists within the sphere ($V=(4/3)\pi *$(longest radius)*(short radius)$^2$). To calculate the periplasmic volume, the cytoplasmic volume is subtracted from the total volume of the cell.

Protein Expression and Quantification:
*E. coli* BL21(DE3) (NEB product #c2527) containing pET28a (emd Millipore product #69864) and its derivatives carrying GFP or collagen derivatives were grown in a shaking incubator at 37° C. overnight in switch media containing 50 mg/mL kanamycin (p212121 product #2251180). Next day, subcultures are started with a 1:10 dilution of the overnight culture into fresh switch media containing 50 mg/mL kanamycin. The culture is then physiologically switched and protein production is induced simultaneously at an OD 600 of 1 to 1.1 (Read on a Molecular Devices Spectramax M2 microplate reader). The physiologically switch and protein production are flipped through the addition of 100 ug/mL Carbenicillin, 50 ug/mL Fosfomycin, and 100 ug/mL IPTG (p212121 product #367-93-1). Protein expression is continued in the switched state from between 8 hours to overnight at room temperature (approximately 22° C.) on an orbital shaker. In order to quantify total protein levels, Quick Start™ Bradford Protein Assay was used on mixed portion of culture and standard curves are quantitated on a Molecular Devices Spectramax M2 microplate reader. In order to quantitate the relative intensity of target protein production relative to the rest of the protein population the mixed portion of the cultures were run on Mini-PROTEAN® TGX™ Gels and stained with Bio-Safe™ Coomassie Stain.

Induction of Protein Production:
Standard procedures have been followed to induce protein production in the physiological state. We have been using the strain BL21(DE3) containing the plasmid pET28a driving the IPTG/lactose inducible production of recombinant proteins and targeting them to the periplasmic space using the DsbA signal sequence. Using the GFP protein, targeted to the periplasmic space as described above, we have demonstrated the ability to gain and increase of 5-fold in protein production when compared to un-switched cell populations induced at the same optical density, for the same amount of time (figures). The induction was optimal at an OD600 of 1.1 and induction was continued for 10 hours at which point the protein produced was measured at about 200 mg/mL.

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments described herein have been described herein for purposes of illustration, various modifications may be made without deviating from the spirit and scope described herein. Accordingly, the disclosure is not limited except as by the appended claims.

What is claimed is:

1. A method of producing collagen comprising:
   a) culturing a recombinant Gram-negative bacterial cell in a medium comprising a magnesium salt, wherein the concentration of magnesium ions in the medium is at least about 6 mM, and wherein the recombinant Gram-negative bacterial cell comprises an exogenous gene encoding the collagen;
   b) inhibiting peptidoglycan biogenesis in the recombinant Gram-negative bacterial cell; and
   c) harvesting the collagen from the medium,
   wherein the inhibiting of b) comprises adding an antibiotic to the medium, wherein the antibiotic inhibits peptidoglycan biogenesis in the recombinant Gram-negative bacterial cell.

2. The method of claim 1, wherein the recombinant Gram-negative bacterial cell is selected from the group consisting of: gammaproteobacteria and alphaproteobacteria.

3. The method of claim 2, wherein the recombinant Gram-negative bacterial cell is selected from the group consisting of: *Escherichia coli, Vibrio natriegens, Pseudomonas fluorescens, Caulobacter crescentus, Agrobacterium tumefaciens*, and *Brevundimonas diminuta*.

4. The method of claim 2, wherein the recombinant Gram-negative bacterial cell is *Escherichia coli*.

5. The method of claim 1, wherein the medium further comprises an osmotic stabilizer.

6. The method of claim 1, wherein the recombinant Gram-negative bacterial cell comprises an expression vector comprising the exogenous gene.

7. The method of claim 1, wherein the method further comprises inducing expression of the exogenous gene.

8. The method of claim 1, wherein the recombinant Gram-negative bacterial cell further comprises a nucleic acid sequence encoding a signal peptide operably linked to the exogenous gene, wherein the signal peptide directs cotranslational export of the collagen from the cytoplasm to the periplasm.

9. The method of claim 8, wherein the signal peptide is a periplasmic disulfide bond oxidoreductase.

10. The method of claim 1, wherein the collagen is human collagen.

11. The method of claim 1, wherein the harvesting of c) comprises clarifying the medium by centrifugation, filtration, or a combination thereof.

12. The method of claim 1, wherein a yield of the collagen is about 1 g/L medium to about 500 g/L medium.

13. The method of claim 1, wherein the recombinant Gram-negative bacterial cell has a periplasm and a cytoplasm, wherein a ratio of a periplasmic volume to a cytoplasmic volume is between about 0.5:1 and about 10:1.

14. The method of claim 1, wherein the recombinant Gram-negative bacterial cell is a coccus having a longest dimension of about 2 µm to about 16 µm.

15. The method of claim 1, wherein the antibiotic is selected from the group consisting of: a β-lactam antibiotic, a phosphonic acid antibiotic, a polypeptide antibiotic, and a glycopeptide antibiotic.

16. The method of claim 15, wherein the β-lactam antibiotic is selected from the group consisting of: a penicillin, a cephalosporin, a carbapenem, and a monobactam.

17. The method of claim 1, wherein the antibiotic is selected from the group consisting of: alafosfalin, amoxicillin, ampicillin, aztreonam, bacitracin, carbenicillin, cefamandole, cefotaxime, cefsulodin, cephalothin, fosmidomycin, methicillin, nafcillin, oxacillin, penicillin g, penicillin v, fosfomycin, primaxin, and vancomycin.

18. The method of claim 1, wherein the inhibiting of b) comprises adding at least two structurally distinct antibiotics to the medium, wherein the at least two structurally distinct antibiotics inhibit peptidoglycan biogenesis in the recombinant Gram-negative bacterial cell.

19. The method of claim 18, wherein the at least two structurally distinct antibiotics inhibit different components of a peptidoglycan biogenesis pathway in the recombinant Gram-negative bacterial cell.

20. The method of claim 1, wherein the recombinant Gram-negative bacterial cell is free of a marker encoding for resistance to an inhibitor of bacterial cell peptidoglycan biogenesis.

21. The method of claim 6, wherein the medium comprises an antibiotic that selects for the presence of the expression vector, wherein the antibiotic that selects for the presence of the expression vector is not an inhibitor of a component of peptidoglycan biogenesis in the recombinant Gram-negative bacterial cell.

22. The method of claim 5, wherein the osmotic stabilizer is a sugar, a betaine, or a combination thereof.

23. The method of claim 22, wherein the sugar is selected from the group consisting of: arabinose, glucose, and sucrose.

24. The method of claim 22, wherein the betaine is trimethylglycine.

25. The method of claim 5, wherein a concentration of the osmotic stabilizer in the medium is between 5% w/v to 20% w/v.

* * * * *